United States Patent

Kori et al.

[11] Patent Number: 5,852,528
[45] Date of Patent: Dec. 22, 1998

[54] VIDEO INFORMATION RECORDING METHOD WHICH USES A COMPARISON OF EVENT INFORMATION IN TWO RECORDED INFORMATION PACKETS

[75] Inventors: Teruhiko Kori, Kanagawa; Masaki Oguro, Tokyo; Ken Iizuka, Kanagawa, all of Japan

[73] Assignee: Sony Corporation, Tokyo, Japan

[21] Appl. No.: 774,898

[22] Filed: Dec. 27, 1996

Related U.S. Application Data

[63] Continuation of Ser. No. 284,106, Aug. 2, 1994, abandoned.

[30] Foreign Application Priority Data

Aug. 24, 1993 [JP] Japan ................................ 5-209622

[51] Int. Cl.$^6$ .................................................... G11B 15/18
[52] U.S. Cl. ................................ 360/69; 360/13; 386/52
[58] Field of Search .............................. 360/13, 69, 132, 360/133; 386/55, 52; 369/273, 291

[56] References Cited

U.S. PATENT DOCUMENTS

| | | | |
|---|---|---|---|
| 4,280,159 | 7/1981 | Nakayama | 360/137 |
| 4,338,644 | 7/1982 | Staar | 360/132 |
| 4,339,776 | 7/1982 | Länger et al. | 360/69 |
| 4,383,285 | 5/1983 | Staar | 360/132 |
| 4,723,181 | 2/1988 | Hickak | 360/132 X |
| 4,814,924 | 3/1989 | Ozeki | 369/291 X |
| 4,991,040 | 2/1991 | Fukuda et al. | 360/137 X |
| 5,132,947 | 7/1992 | Kameda et al. | 369/291 X |
| 5,291,301 | 3/1994 | Lee | 360/14.1 X |
| 5,296,884 | 3/1994 | Honda et al. | 354/106 |
| 5,428,774 | 6/1995 | Takahashi et al. | 360/14.1 X |
| 5,625,739 | 4/1997 | Kotani | 360/13 X |

FOREIGN PATENT DOCUMENTS

PCT/GB89/00393  11/1989  WIPO.

Primary Examiner—Aristotelis M. Psitos
Assistant Examiner—Larry T. Cullen
Attorney, Agent, or Firm—Frommer Lawrence & Haug LLP; William S. Frommer

[57] ABSTRACT

Video information records are recorded in a small capacity memory included in a tape cassette under the control of a system controller supplied with date information from a calendar circuit, clock information from a clock circuit, place information from a GPS (global positioning system) circuit, and scene setting information from a scene setting switch of an operation unit (such as a video camera). When video information is recorded by using the date information, for example, the system controller uses that date information as well as date information previously stored in the memory to process the just-recorded video information record.

16 Claims, 12 Drawing Sheets

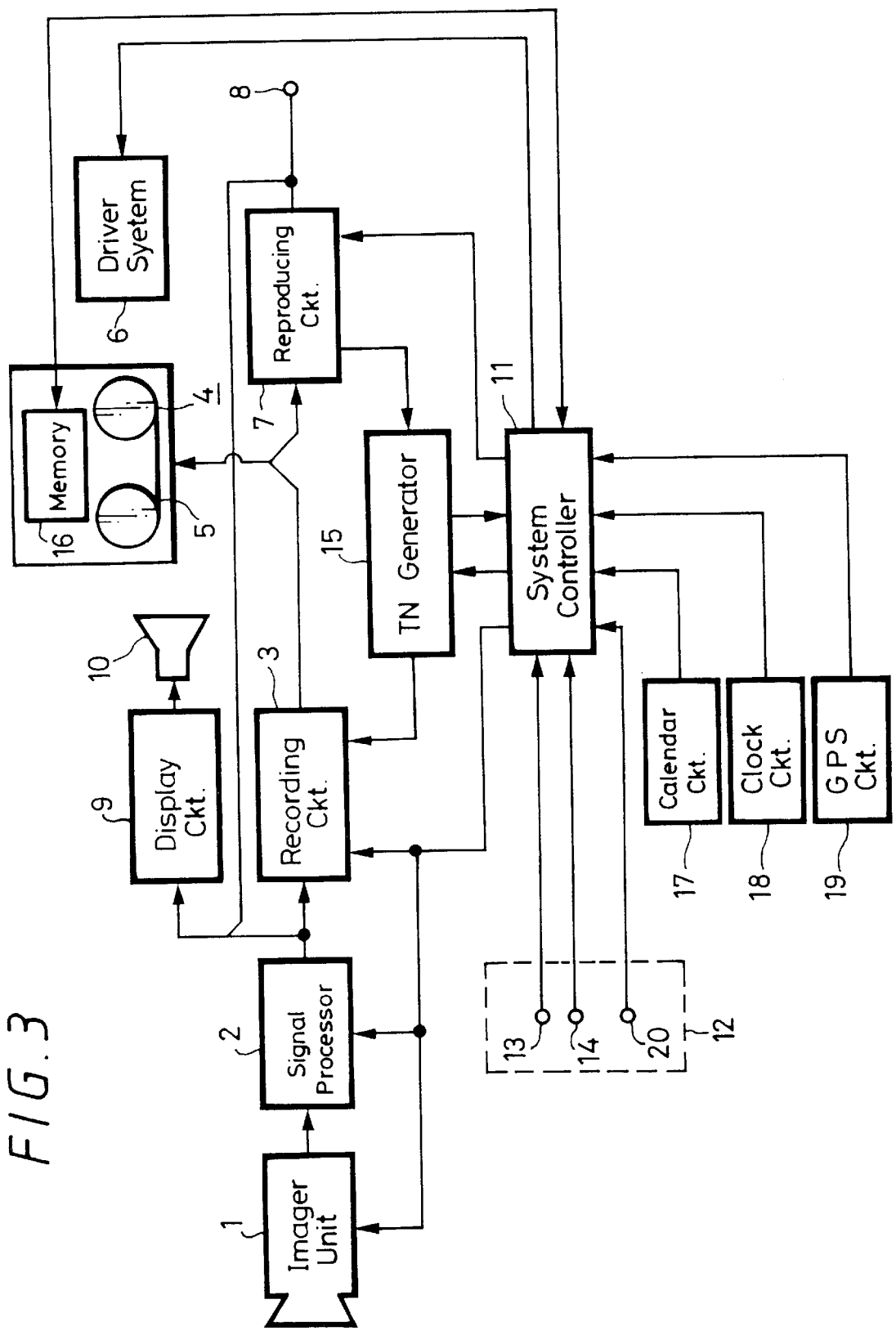

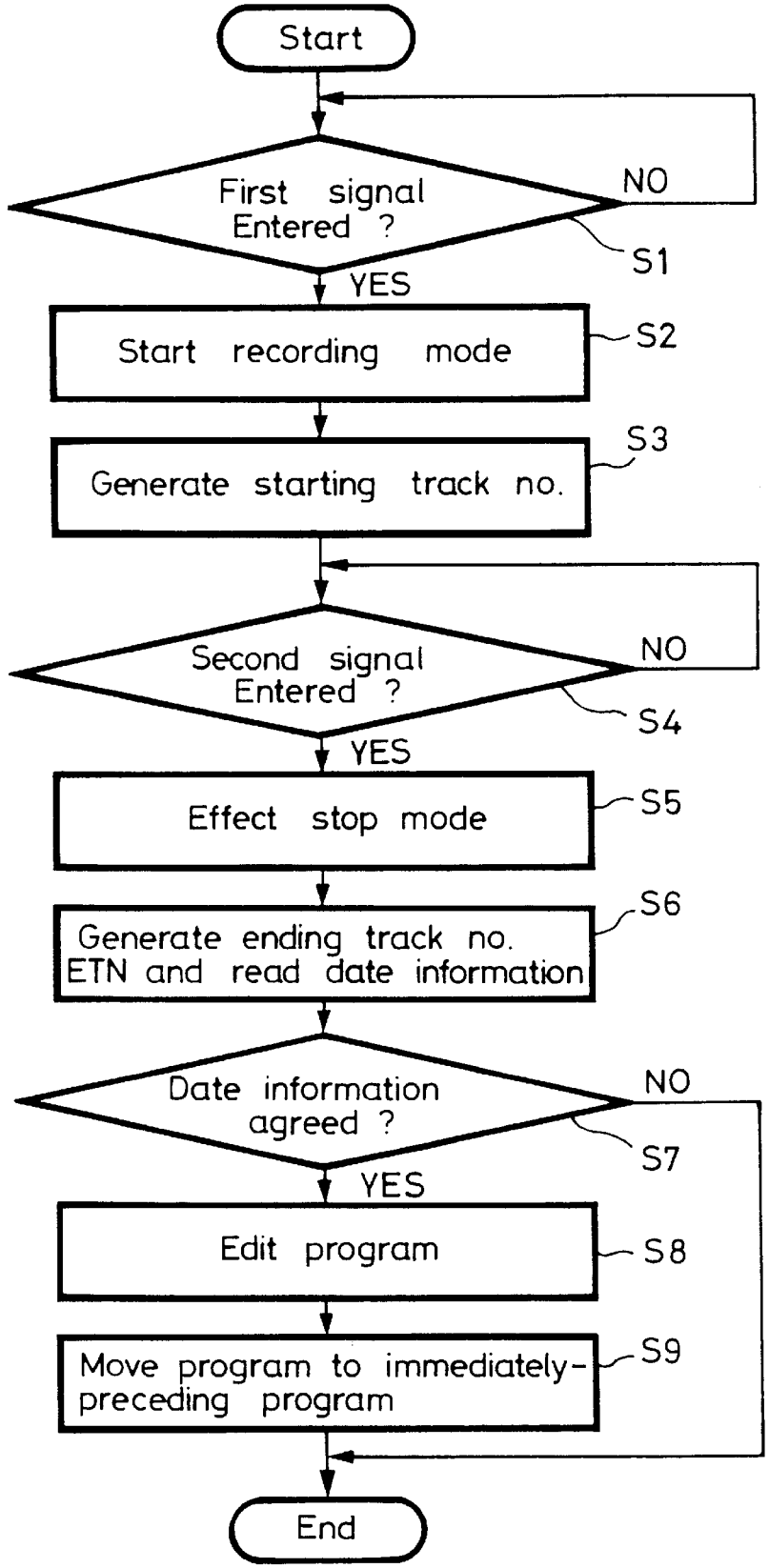

BTN
ETN
Date
Program
Hierarchic
Packet

BTN
ETN
Date
Program
Hierarchic
Packet

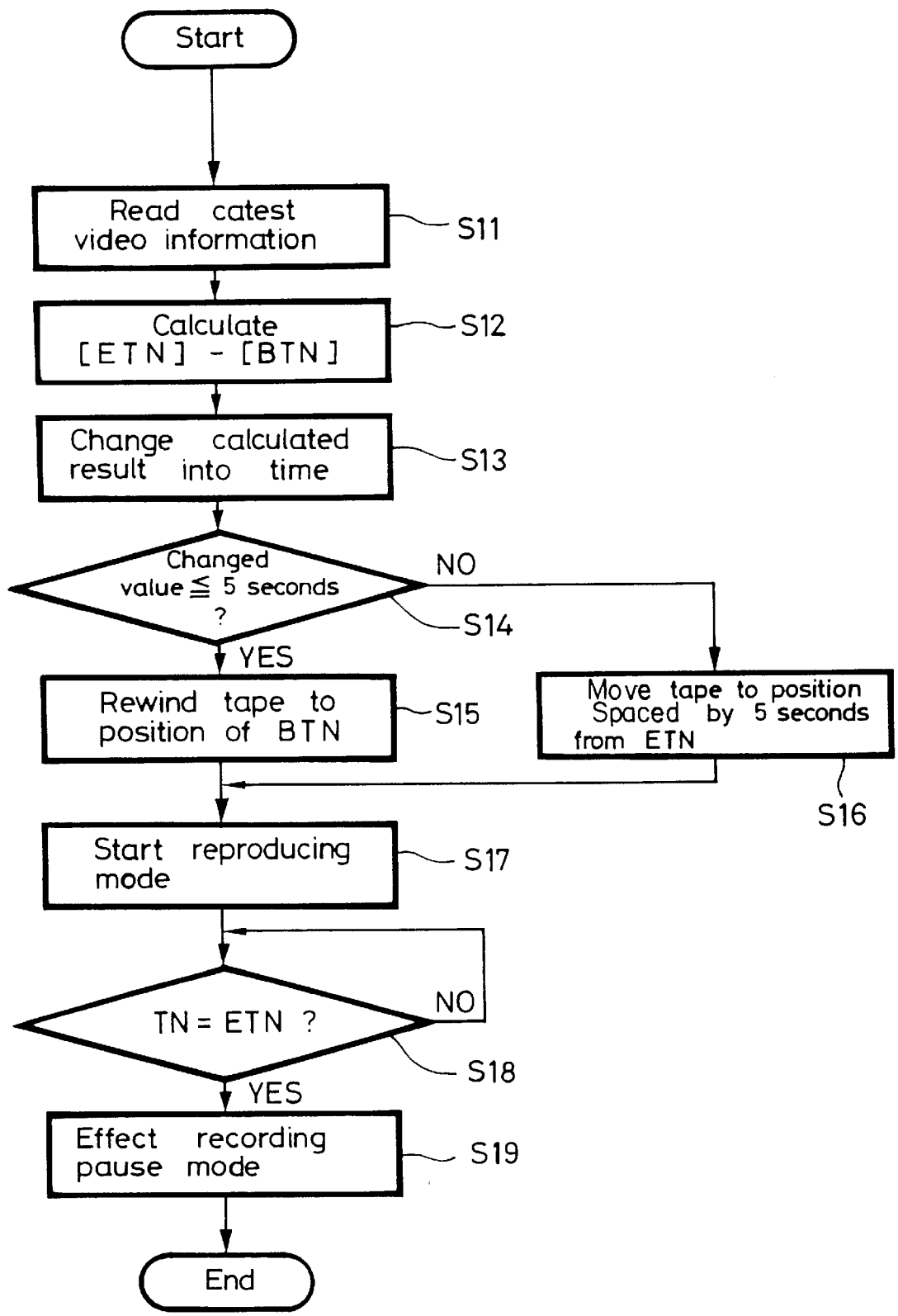

VIDEO INFORMATION RECORDING METHOD WHICH USES A COMPARISON OF EVENT INFORMATION IN TWO RECORDED INFORMATION PACKETS

This application is a continuation of application Ser. No. 08/284,106, filed Aug. 2, 1994 now abandoned.

BACKGROUND OF THE INVENTION

1. Field of the Invention

The present invention relates to a video information recording method for use in recording video information in a memory mounted on a tape cassette of a VCR (video cassette recorder), for example.

2. Description of the Related Art

U.S. Pat. No. 4,338,644 and U.S. Pat. No. 4,383,285 describe methods in which a memory is mounted on a tape cassette of a VCR and video information is recorded in this memory.

In Japanese patent application No. H04-217503 and corresponding EP application No. 0,580,434 (laid-open on Jan. 26, 1994) are disclosed such recording medium cassettes. Each of the above applications is owned by the assignee of the present invention and is hereby incorporated by references.

When video information is recorded in a memory mounted on a tape cassette of VCR, or when video information is recorded by a VCR of a single-unit video camera-recorder type, for example, a starting track number and an ending track number can be recorded in a ganged relation to operation of a recording operation switch each time a recording of video information is implemented.

However, when the video information is recorded on the memory mounted on the tape cassette of the VCR, if a memory capacity is 4 kbits, then about 30 data can be recorded on the memory together with only the starting track number and the ending track number. In this case, if character information or the like is recorded on the memory together with video information, then about 10 data can be recorded on the memory.

In that case, if the starting track number and the ending track number are recorded in the memory by the VCR of the single-unit video camera-recorder type each time a recording of video information is implemented, there is then the risk that the number of recorded video data will exceed 30. Although the number of video data to be recorded can be increased by increasing the capacity (size) of the memory, such increase is limited because the memory must be small enough to be mounted on mass-produced tape cassettes.

SUMMARY OF THE INVENTION

In view of the aforesaid aspect, it is an object of the present invention to provide a video information recording method in which video information can be recorded in a small capacity memory for a long period of time.

According to an aspect of the present invention, there is provided a video information recording method which records video information composed of at least a recording starting track number, a recording ending track number and event information. The video information recording method comprises the steps of comparing event information in the recorded video information, and editing and recording the recorded video information in response to the compared result.

In accordance with another aspect of the present invention, there is provided a tape cassette having a first recording medium as a main recording medium and a second recording medium as a sub-recording medium. This tape cassette comprises a cassette housing for housing the first and second recording media, and an interface for receiving information from a recording or reproducing apparatus, wherein video information composed of at least a recording starting track number, a recording ending track number and event information is recorded on the second recording medium, event information of the recorded video information are compared with each other and the video information is edited and recorded in response to the compared result.

BRIEF DESCRIPTION OF THE DRAWINGS

FIG. 3 is a block diagram showing an arrangement of an example of an apparatus to which reference will be made in explaining a video information recording method according to the present invention;

FIG. 4 is a flowchart to which reference will be made in explaining operation of the apparatus shown in FIG. 3;

FIG. 7 is a flowchart to which reference will be made in explaining operation of how to confirm the content of video data;

DETAILED DESCRIPTION OF THE PREFERRED EMBODIMENT

The present invention will now be described with reference to the drawings.

Figure 1:
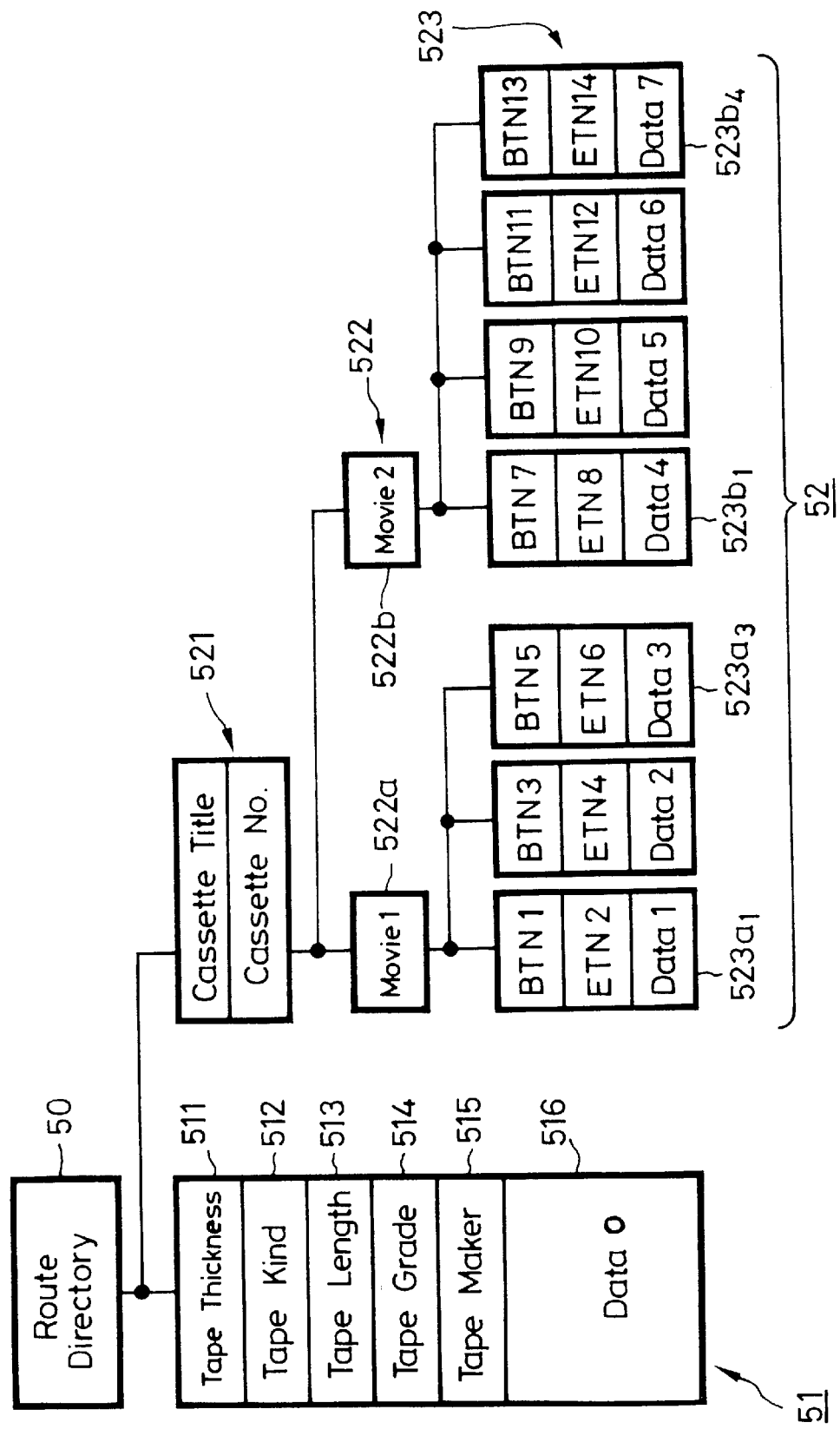
FIG. 1 is a diagram showing video data recorded in a memory.

FIG. 1 of the accompanying drawings shows data recorded in a memory. As shown in FIG. 1, data are recorded in the memory in the form of a so-called tree structure (i.e., hierarchic structure) composed of a plurality of hierarchic packets. A route directory 50 is followed by a recording medium information directory 51 and a recording content information directory 52.

The recording medium information directory 51 includes tape thickness data 511, tape kind data 512, tape length data 513, tape grade data 514 and tape maker data 515. The tape maker data 515 is followed by data that is determined based on the tape maker data 515. The recording medium information directory is indispensable for each tape cassette.

The recording content information directory 52 is provided in the form of a hierarchic structure, and composed of a highest-order hierarchic packet 521, a title hierarchic packet 522 and a program hierarchic packet 523. The highest-order hierarchic packet 521 includes cassette title information and cassette number information. The highest-order hierarchic packet 521 also is indispensable for each tape cassette.

A title hierarchic packet 522 is provided under the highest-order hierarchic packet 521. There are provided a plurality of title hierarchic packets 522. Titles, such as "MOVIE 1" and "MOVIE 2" are recorded on respective title hierarchic packets 522*a*, 522*b*.

A program hierarchic packet 523 is provided under the title hierarchic packet 522. The program hierarchic packet 523 is composed of a plurality of program hierarchic packets, i.e., program hierarchic packets 523*a*1 to 523*a*3 and 523*b*1 to 523*b*4. Each of the program hierarchic packets 523*a*1 to 523*a*3; and 523*b*1 to 523*b*4 includes a recording start track number BTN, a recording ending track number ETN of the recording unit and event data associated with the program packets at every event recording unit of each title.

Figure 2:
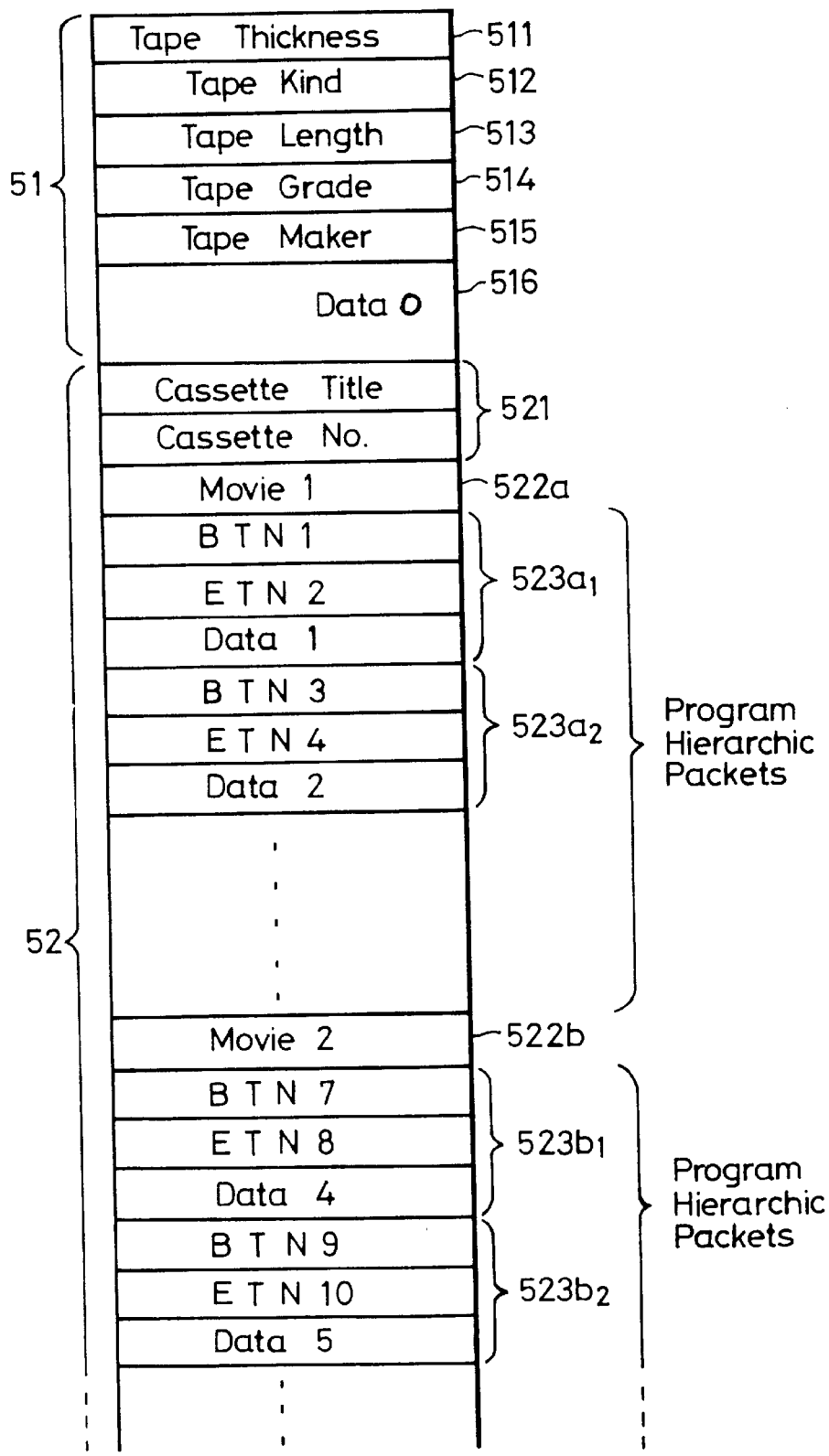
FIG. 2 is a diagram used to explain how to store data shown in FIG. 1 in the addresses of the memory in actual practice.

FIG. 2 show an arrangement used when data shown in FIG. 1 are stored in the addresses of the memory in actual practice. As shown in FIG. 2, there is recorded the recording medium information directory 51 composed of the tape thickness data 511, the tape kind data 512, the tape length data 513, the tape grade data 514, the tape maker data 515 and the data 516 from the small memory address, in that order.

The recording medium information directory 51 is followed by the recording content information directory 52. The recording content information directory 52 includes the highest-order hierarchic packet 521 formed of a cassette title and a cassette number. The highest-order hierarchic packet 521 is followed by the title hierarchic packet 522*a*, the program hierarchic packets 523*a*1 to 523*a*3, the title hierarchic packet 522*b* and the program hierarchic packets 523*b*1 to 523*b*4, in that order.

Specifically, the title hierarchic packet 522*a* representing "MOVIE 1", for example, is followed by the program hierarchic packets 523*a*1 to 523*a*3 representing every event unit of the "MOVIE 1" and the program hierarchic packets 523*b*1 to 523*b*4 representing every event unit of the "MOVIE 2", in that order.

In this way, the titles of the recorded contents and the recording information (recording content information), such as the recording starting track number BTN and the recording ending track number ETN of every recording unit of the title can be recorded on the memory mounted on the tape cassette of the VCR.

FIG. 3 is a block diagram showing a hardware arrangement used when the video information recording method according to the present invention is realized by the VCR of the single-unit video camera-recorder type, for example. As shown in FIG. 3, a video signal from an imaging unit 1 is supplied through a signal processor 2 to a recording circuit 3 and thereby recorded on a magnetic tape 5 incorporated within a tape cassette 4. A driver system 6 transports the magnetic tape 5 and drives a rotary magnetic head (not shown). Although specific mechanisms used upon recording are not shown, they are substantially the same as those of the conventional VCR and therefore need not be described.

A signal reproduced from the magnetic tape 5 by a rotary magnetic head (not shown) is supplied to a reproducing circuit 7 and a signal from the reproducing circuit 7 is developed at an output terminal 8. The signal from the signal processor 2 or the reproducing circuit 7 is supplied through a display circuit 9 to a viewfinder 10 which displays thereon a picked-up or reproduced video signal. The above-mentioned mechanism and circuits are controlled by a system controller 11 formed of a microcomputer, for example.

Specifically, when a first signal is entered and supplied to the system controller 11 by a recording operation switch 13 (start/stop switch) of an operation unit 12, for example, the above-mentioned mechanism and circuits are set to the recording mode so that the video signal from the imaging unit 1 is recorded on the magnetic tape 5. When a second signal is entered and supplied to the system controller 11, the above-mentioned mechanism and circuits are set to the stop mode. Therefore, each time the first or second signal is entered and supplied to the system controller 11 by the operation switch 13, the above-mentioned mechanism and circuits are alternately placed in the recording or stop mode.

When a signal from a recording confirmation operation switch 14 of the operation unit 12 is entered and supplied to the system controller 11, the above-mentioned mechanism and circuits are set in the reproducing mode and the magnetic tape 5 is rewound by a predetermined amount, whereby a video signal reproduced from the magnetic tape 5 at its rewound position is displayed on the viewfinder 10. Further, other operation is carried out under the control of the system controller 11. The respective operation switches 13, 14 of the operation unit 12 are disposed on respective predetermined portions of the apparatus.

So-called consumer digital VCRs record consecutive track numbers (TN) from the recording starting end of the magnetic tape 5 at every track. In the above-mentioned digital VCR, the track number (TN) reproduced by the reproducing circuit 7 is supplied to a track number generator (simply referred to as "TN generator") 15, and track number (TN) data generated by the TN generator 15 is supplied to the recording circuit 3. Thus, the consecutive track numbers (TN) are recorded on the magnetic tape 5 at every track.

The TN generator 15 generates the track number (TN) data from a predetermined reference value when the magnetic tape 5 is recorded from its recording starting end. The TN generator 15 generates the track number (TN) from the track number value reproduced from the immediately-preceding track when the magnetic tape 5 is recorded from its intermediate portion. Further, when the immediately-preceding track is not reproduced while the magnetic tape 5 is recorded from its intermediate portion, the wound tape diameter of the magnetic tape 5 housed within the tape cassette 4 is detected and the TN generator 15 generates a track number (TN) calculated from the detected value of the wound tape diameter of the magnetic tape 5.

In the above-mentioned apparatus, the memory 16 is mounted in the tape cassette 4 and video information is recorded in the memory 16. Specifically, the recording of data in the memory 16 is implemented by the system controller 11 that is formed of the microcomputer.

Furthermore, the system controller 11 is supplied with date information from a calendar circuit 17 which generates date information, clock information from a clock circuit 18 which generates clock information, place information from a GPS (global positioning system) circuit 19 which generates place information and scene setting information from a scene setting switch 20 of the operation unit 12. This information supplied to the system controller 11 is collectively referred to herein as the event information.

When video information is recorded by using data information, for example, the system controller 11 carries out the processing in a flowchart shown in FIG. 4 to record video information in the memory 16.

As shown in FIG. 4, following the start of operation, it is determined in decision step S1 whether or not the first signal is entered and supplied to the system controller 11 by the recording operation switch 13. If a YES is the output at decision step S1, then the processing process to step S2, whereat the recording mode is started. If on the other hand a NO is the output at decision step S1, then the decision step S1 is repeated. In the next step S3, a starting track number BTN of a new program is generated.

It is determined in decision step S4 whether or not a second signal is entered and supplied to the system controller 11 by the recording operation switch 13. If a YES is the output at decision step S4, then the processing proceeds to step S5, whereat the above-mentioned mechanism and circuits are placed in the stop mode and the recording is ended. If a NO is the output at decisions step S4, then the decision step S4 is repeated. Then, the processing proceeds to step S6, wherein an ending track number ETN of a new program is generated and date information representing that very day is read out from the calendar circuit 17.

It is determined in decision step S7 whether or not date information of immediately-preceding program and date information of program that precedes the immediately-preceding program agree with each other. If the date information do not agree with each other as represented by a NO at decision step S7, then the processing is ended. If on the other hand the date information agree with each other as represented by a YES at decision step S7, then the processing proceeds to step S8, whereat the immediately-preceding program and the program preceding the immediately-preceding program are edited. Then, the processing proceeds to the next step S9, whereat the new program is moved to the immediately-preceding program. Then, the processing is ended.

Figure 5A:
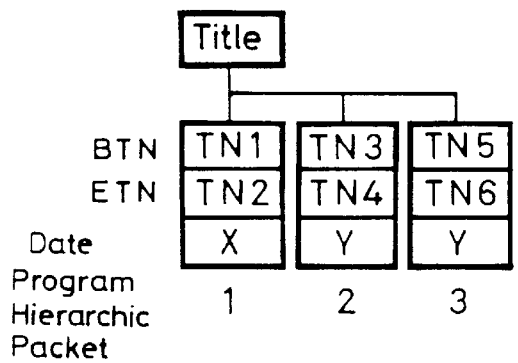
FIGS. 5A through 5G are diagrams used to explain the data structure of video data recorded when a new recording is carried out with data representative of a new date, respectively.
Figure 5B:
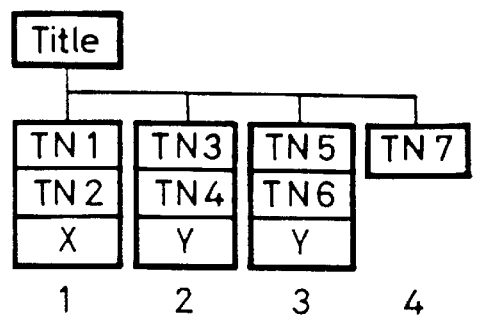
Figure 5C:
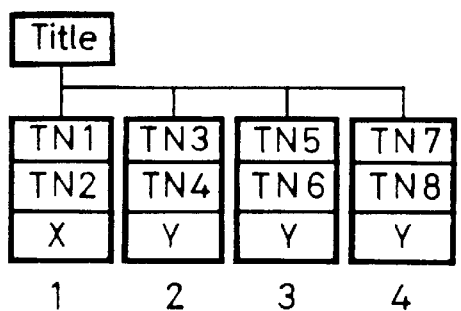

Therefore, according to this operation, in the initial state, as shown in FIG. 5A, the program hierarchic packet 1 of date X is recorded on the tape from the starting track number TN1 to the ending track number TN2; and the program hierarchic packets 2, 3 of date Y are recorded on the tape from the starting track numbers TN3 and TN5, respectively, to the ending track numbers TN4 and TN6, respectively. In this state, when a new recording is started with the same date Y as shown in FIG. 5B, a new recording starting track number TN7 is memorized in a new program hierarchic packet 4. Subsequently, when this new recording is ended, as shown in FIG. 5C, a new recording ending track number TN8 and a date Y are memorized in the program hierarchic packet 4.

Further, in this state, it is determined whether or not date information of the immediately-preceding program hierarchic packet 3 and date information of the program hierarchic packet 2 which precedes the immediately-preceding program hierarchic packet 3 agree with each other. In this case, date data Y are the same ("YES") so the immediately-preceding program hierarchic packet 3 and the program hierarchic packet 2 which precedes the immediately-preceding program hierarchic packet 3 are edited.

Figure 5D:
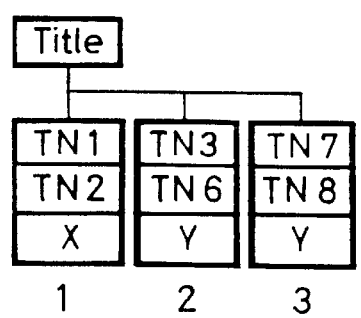

Specifically, the recording starting track number TN3 of the program hierarchic packet 2, the recording ending track number TN6 of the program hierarchic packet 3 and the date data Y are memorized in the program hierarchic packet 2. Further, the content of the program hierarchic packet 4 is moved to the program hierarchic packet 3, whereby the recording shown in FIG. 5D is carried out.

Figure 5E:
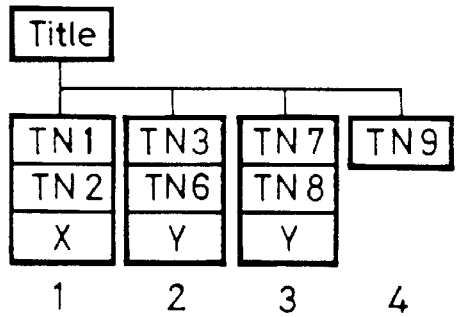
Figure 5F:
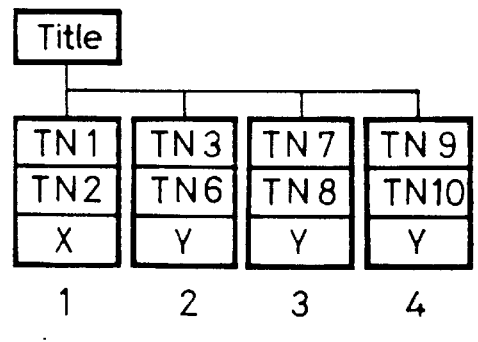
Figure 5G:
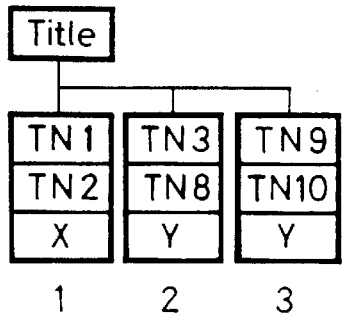

In this state, when a new recording is carried out with the same date Y, new program hierarchic packets are recorded as shown in FIGS. 5E to 5G. In this case, even when the new recording is carried out with the same date data Y, the number of the program hierarchic packets is constantly limited to four.

Figure 6A:
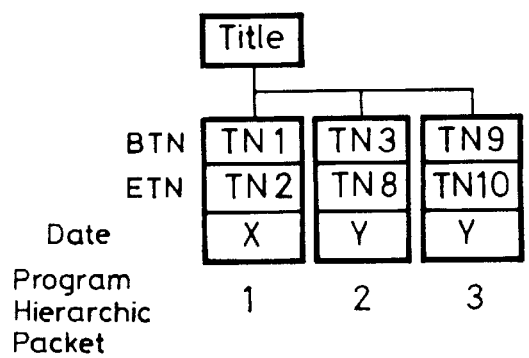
FIGS. 6A through 6I are diagrams used to explain data structure of video data recorded when a new recording is carried with data representative of a new date, respectively.
Figure 6B:
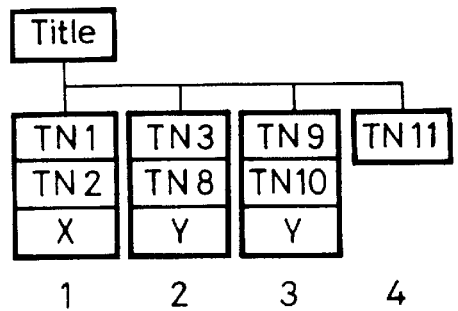
Figure 6C:
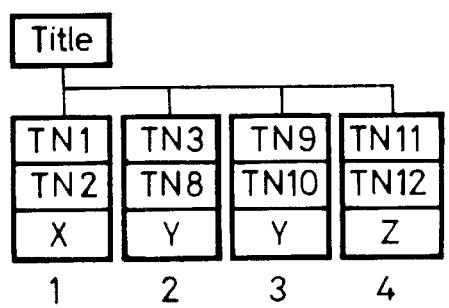

When a new recording is carried out with other date data Z, as shown in FIG. 6A, the state shown in FIG. 5G is used as the initial state and a new recording starting track number TN11 is memorized in the program hierarchic packet as shown in FIG. 6B. After the new recording is completed, a new recording ending track number TN12 and the date data Z are memorized in the program hierarchic packet 4 as shown in FIG. 6C.

In this state, it is determined whether or not the date data of the immediately-preceding program hierarchic packet 3 and the program hierarchic packet 2 which precedes the immediately-preceding program packet 3 agree with each other. Since the two date data Y are the same ("YES"), the immediately-preceding program hierarchic packet 3 and the program hierarchic packet 2 which precedes the immediately-preceding program hierarchic packet 3 are edited.

Figure 6D:
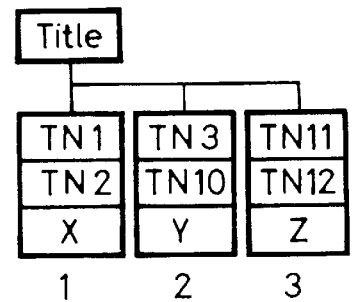

Specifically, the recording starting track number TN3 of the program hierarchic packet 2, the recording ending track number TN10 of the program hierarchic packet 3 and the date data Y, for example, are memorized in the program hierarchic packet 2. Further, the content of the program hierarchic packet 4 is moved to the program hierarchic packet 3. Therefore, the recording shown in FIG. 6D is carried out.

Figure 6E:
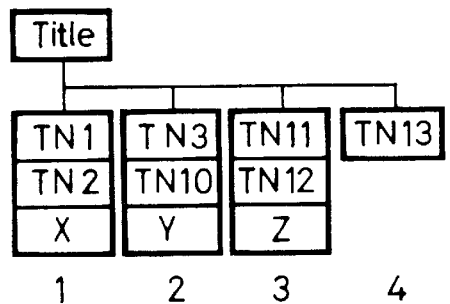
Figure 6F:
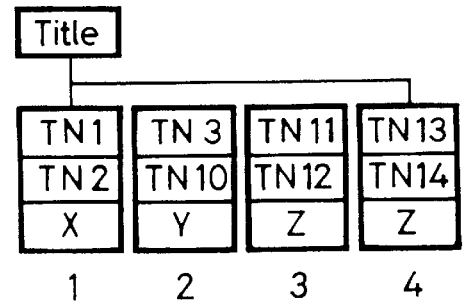

Under this state, when a new recording is carried out with the date Z, a new recording starting track number TN13 is memorized in the program hierarchic packet 4 as shown in FIG. 6E. Then, when this new recording is completed, a new recording ending track number TN15 and the date data Z are memorized in the program hierarchic packet 4 as shown in FIG. 6F.

Under this state, it is determined whether or not date data of the immediately-preceding program hierarchic packet 3 and date data of the program hierarchic packet 2 which precedes the immediately-preceding program hierarchic packet 3 agree with each other. Since the date data are different ("NO"), the program hierarchic packets 2, 3 are preserved as they are. Specifically, a recording shown in FIG. 6F is preserved.

Figure 6G:
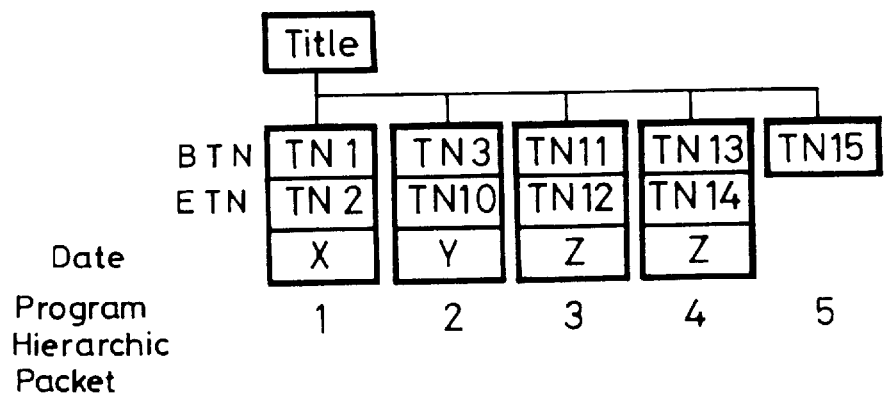
Figure 6H:
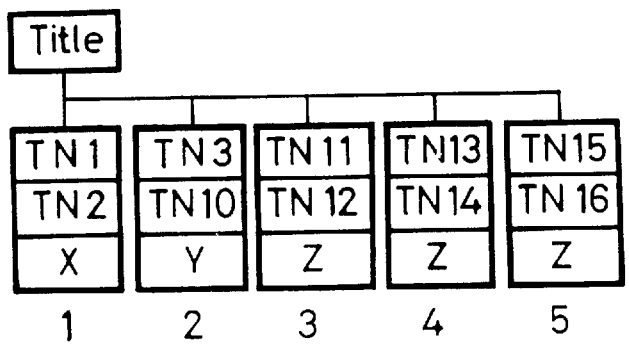

Further, under this state, when a new recording is started with the date data Z, a new recording starting track number TN15 is memorized in a program hierarchic packet 5 as shown in FIG. 6G. When this new recording is completed, a new recording ending track number TN16 and the date data Z are memorized in the program hierarchic packet 5 as shown in FIG. 6H.

Under the state, it is determined whether or not the date data of the immediately-preceding program hierarchic packet 4 and the date data of the program hierarchic packet 3 which precedes the immediately-preceding program hierarchic packet 4 agree with each other. Since the date data are the same ("YES"), the immediately-preceding program hierarchic packet 4 and the program hierarchic packet 3 which precedes the immediately-preceding program hierarchic packet 4 are edited.

Figure 6I:
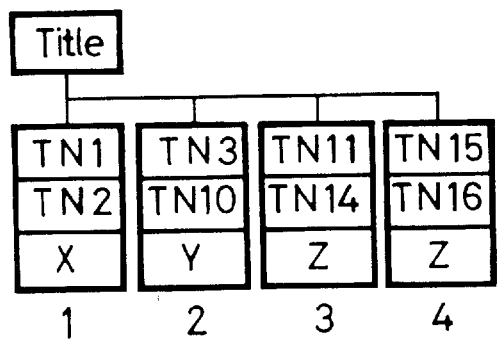

Specifically, the recording starting track number TN11 of the program hierarchic packet 3, the recording ending track number TN14 of the program hierarchic packet 4 and the date data Z are memorized in the program hierarchic packet 3. Further, the content of the program hierarchic packet 5 is moved to the program hierarchic packet 4. Thus, a recording shown in FIG. 6I, for example, is effected.

In this way, video information is recorded by using date information. In this case, even when a new recording is effected with the same date data, the number of the program hierarchic packets is constantly limited to "number of date data+2". Therefore, the number of the recording can be prevented from being increased considerably in a short period of time.

According to the video information recording method of the present invention, since event information in the recorded video information are compared with each other and the video information is edited and recorded in response to the compared result, it is possible to record video information in a small capacity memory for a long period of time.

While the video information is recorded by using the date data from the calendar circuit 17 as described above, the present invention is not limited thereto and the video information can be recorded by using clock information from the clock circuit 18 or place information from the GPS circuit 19.

In that case, at step S6 in the flowchart shown in FIG. 4, instead of the date data from the calendar circuit 17, the clock information from the clock circuit 18 and the place information from the GPS circuit 19 are read out. At the next decision step S7 in the flowchart shown in FIG. 4, it is determined whether or not the clock data of the immediately-preceding program hierarchic packet and the program hierarchic packet that precedes the immediately-preceding program hierarchic packet fall within a predetermined time or whether or not the place data thereof fall within a predetermined range.

Alternatively, it is possible to record the video information in accordance with the user's request. In that case, the information from the scene setting switch 20 of the operation unit 12 is judged at the decision step S7 of the flowchart shown in FIG. 4.

According to the above-mentioned method, since highly-consecutive video information can be edited by using date information, clock information, place information or other information from the operation 12 unit, the video information can be used satisfactorily.

Further, according to the above-mentioned method, latest video information is recorded separately. When the next recording is started, the editing of the video information that is separately recorded is carried out. Therefore, the latest video information is preserved until the next recording is started, whereby the recorded content can be confirmed at any time easily.

FIG. 7 is a flowchart showing operation executed when the recorded content is confirmed during a time period of 5 seconds at maximum. In FIG. 7, operation is started when the signal from the recording confirmation operation switch 14 is supplied to the system controller 11.

As shown in FIG. 7, following the start of operation, latest video information is read out at step S11. In the next step S12, (ending track number ETN)–(starting track number BTN) is calculated. In step S13, a calculated result obtained from step S12 is changed into a time. It is determined in the next decision step S14 whether or not the changed value is shorter than 5 seconds.

If the changed value is shorter than 5 seconds as represented by a YES at decision step S14, then the processing proceeds to step S15, whereat the magnetic tape 5 is rewound to the position of the starting track number BTN of the latest video information. If on the other hand the changed value is longer than 5 second as represented by a NO at decision step S14, then the processing proceeds to step S16, whereat the magnetic tape 5 is moved to a position that is spaced by 5 seconds from the ending track number ETN of the latest video information.

In step S17, the reproducing mode is started. Then, it is determined in the next decision step S18 whether or not the track number TN reproduced at step S17 coincides with the ending track number ETN of the latest video information. If a YES is the output at decision step S18, then the processing proceeds to step S19, wherein the VCR is set in the recording pause mode and the processing is ended. If a NO is the output at decision step S18, then step S18 is repeated.

Therefore, according to the above-mentioned method, since the latest video information is recorded separately, it is possible for the user to confirm the recorded content at any time easily.

Figure 8:
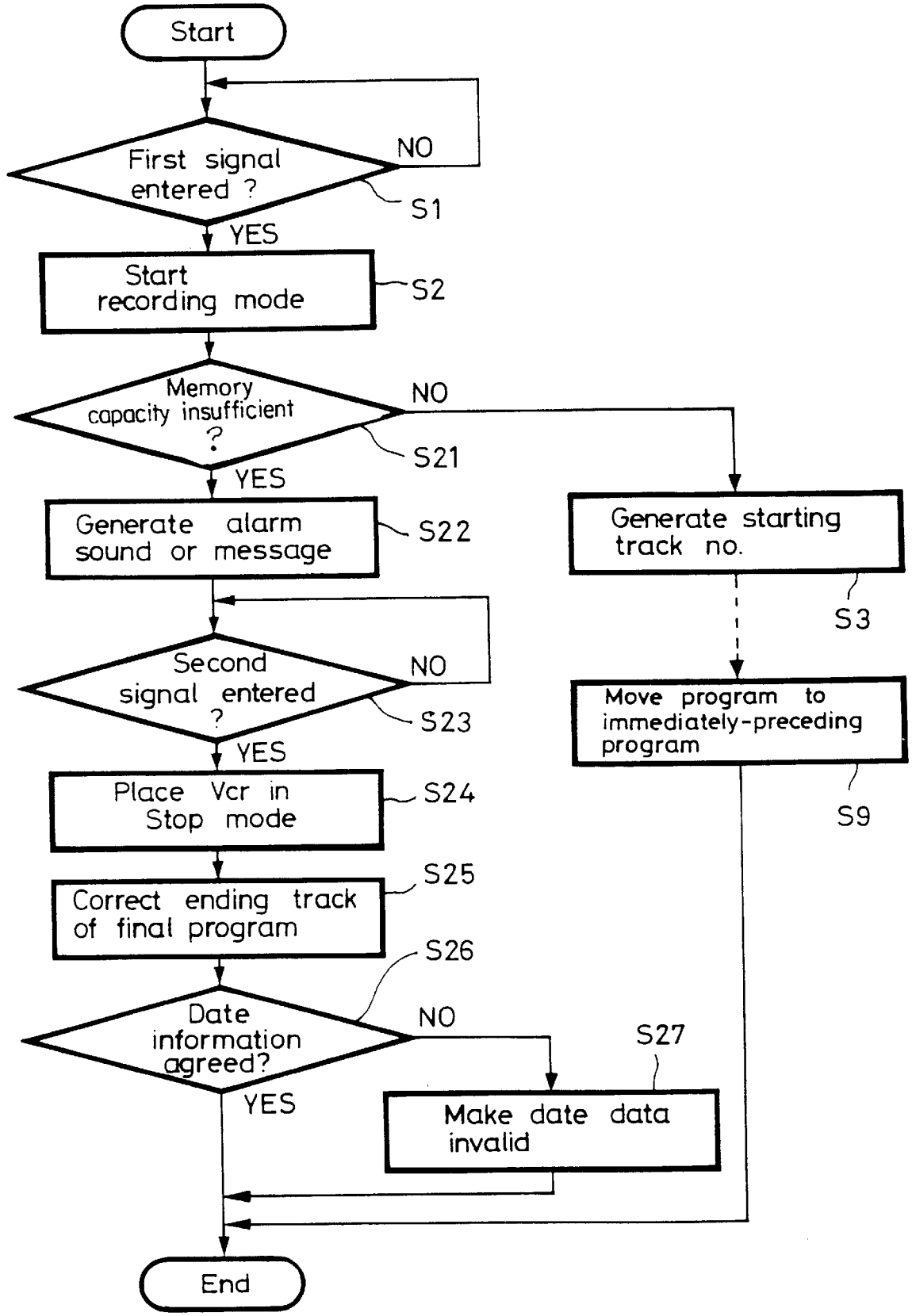
FIG. 8 is a flowchart to which reference will be made in explaining operation implemented when a capacity of a memory is not sufficient.

Further, according to the above-mentioned method, if the capacity of the memory 16 becomes insufficient even during the edit, the following operations as shown in the flowchart in FIG. 8 are carried out. Specifically, when the capacity of the video information recording medium (memory 16) is insufficient, recorded video information is edited after generating an alarm sound or alarm message.

In FIG. 8, the step S2 in the flowchart shown in FIG. 4 is followed by a decision step S21, whereat it is determined whether or not the capacity of the memory 16 is insufficient. If the capacity of the memory 16 is sufficient as represented by a NO at decision step S21, step S3 and the following steps in the flowchart shown in FIG. 4 are executed.

If the capacity of the memory 16 is insufficient as represented by a YES at decision step S21, then the processing proceeds to step S22, whereat an alarm sound or alarm message is generated. Further, it is determined in decision step S23 whether or not the second signal is entered. If a NO is the output at decision step S23, then the VCR is set in the standby mode until the second signal is entered and supplied to the system controller 11 from the recording operation switch 13. If a YES is the output at decision step S23, then the processing proceeds to the next step S24, whereat the VCR is set in the stop mode and the recording is completed. In step S25, an ending track number of the final program is corrected by the ending track number ETN of the new program and date data is read from the calendar circuit 17.

It is determined in decision step S26 whether or not the date data read from the calendar circuit 17 and the date data of the final program agree with each other. If the date data agree with each other as represented by a YES at decision step S26, then the processing is ended. If date data do not agree with each other as represented by a NO at decision step S26, then the processing proceeds to the next step S27, whereat the date data is made invalid and the processing is ended. The date data can be made invalid by recording a meaningless value, such as when binary values constructing the data are all set to "1".

Figure 9A:
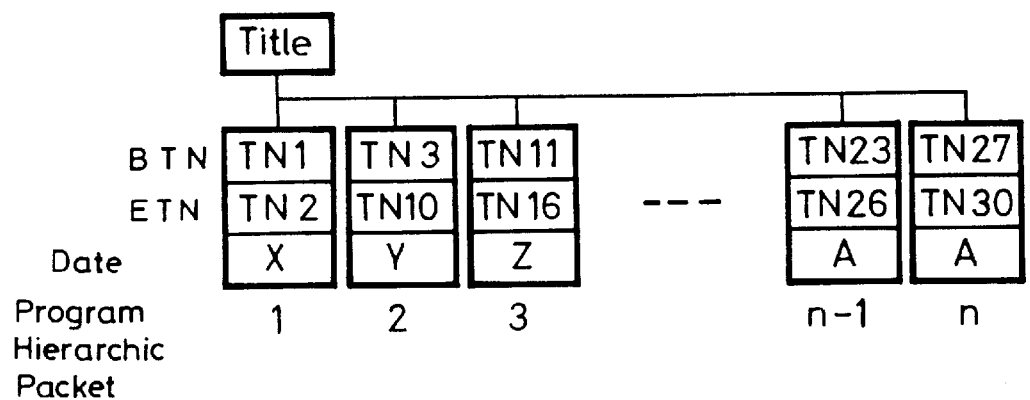
FIGS. 9A through 9C are diagrams used to explain the operation of the flowchart shown in FIG. 8, respectively.
Figure 9B:
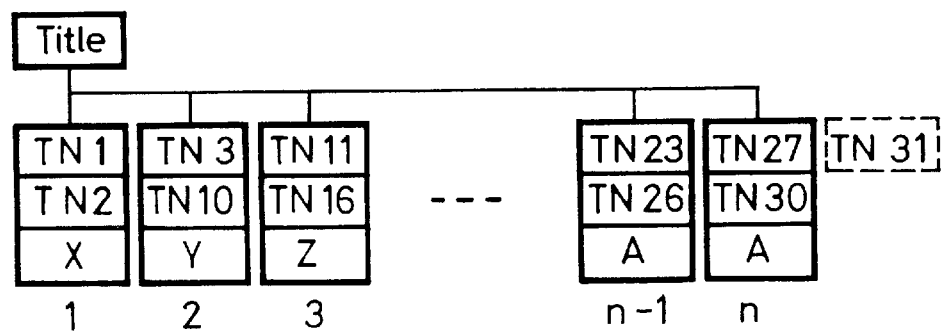
Figure 9C:
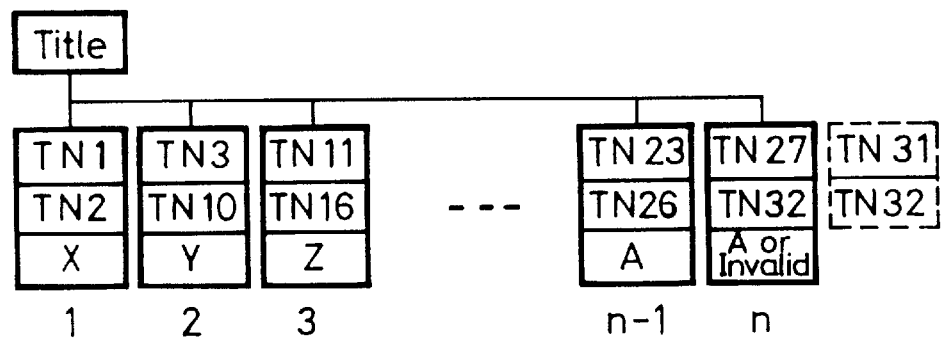

Therefore, if the capacity of the memory 16 is insufficient under the state shown in FIG. 9A, then the new recording starting track number TN31 is generated as shown in FIG. 9B at a timing point at which the new recording is started. When the new recording is ended as shown in FIG. 9C, a new recording ending track number TN32 is generated. Then, the ending track number of the final program hierarchic packet n is corrected by the ending track number TN32.

Under this state, it is determined whether or not the date data of the final program hierarchic packet n and the date data from the calendar circuit 17 agree with each other. If the date data A are the same, the final program hierarchic packet n is preserved as it is. Specifically, the recording shown in FIG. 9C is preserved. If on the other hand the date data A are not the same, date data of the final program hierarchic packet n is made invalid.

Figure 10:
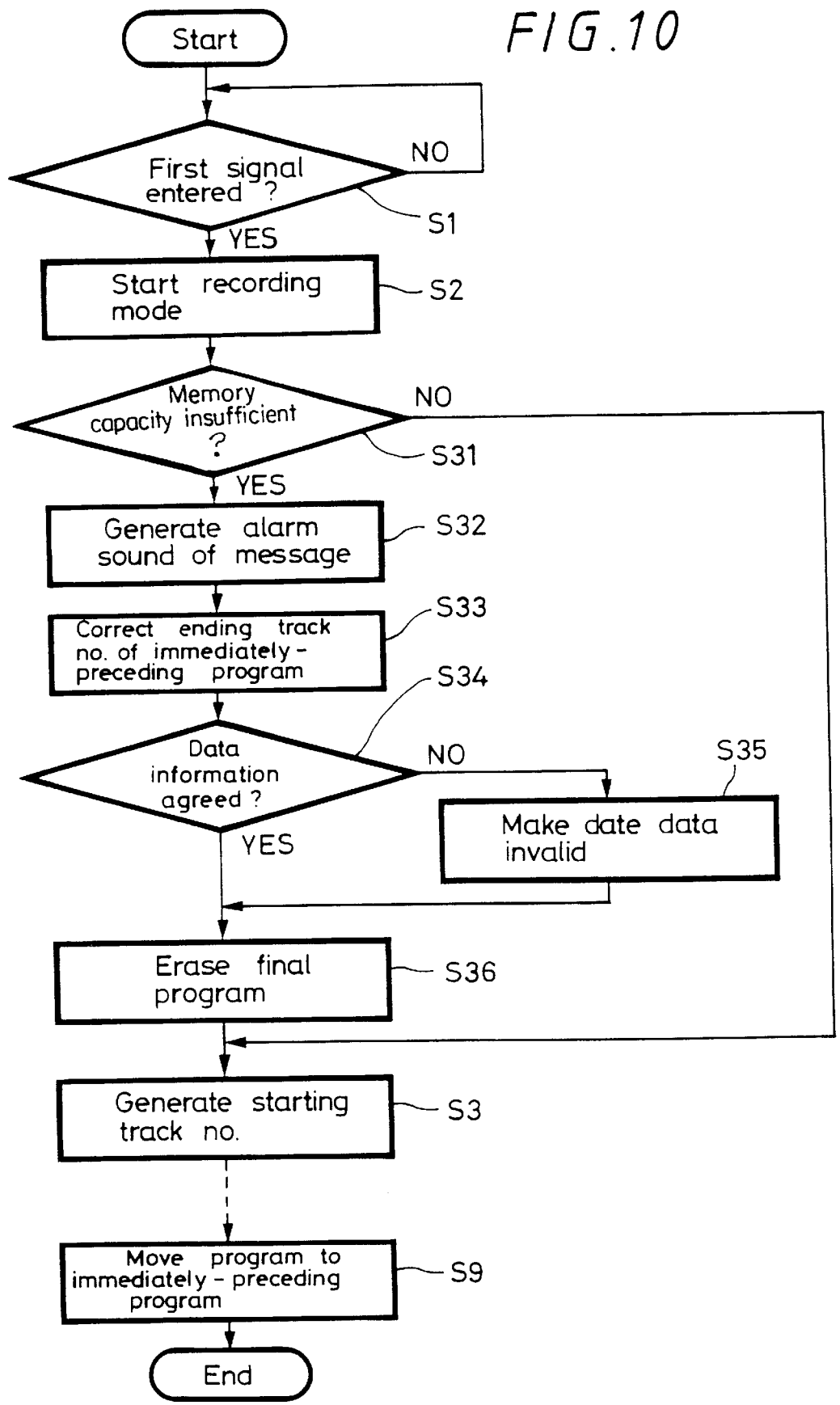
FIG. 10 is a flowchart to which reference will be made in explaining another example of operation implemented when the capacity of the memory is not sufficient.

Alternatively, FIG. 10 is a flowchart showing another example of operations executed when the capacity of the recording medium (memory 16) is not sufficient. In FIG. 10, the step S2 in the flowchart shown in FIG. 4 is followed by decision step S31, whereat it is determined whether or not the capacity of the memory 16 is insufficient. If the capacity of the memory 16 is sufficient as represented by a NO at decision step S31, the step S3 and the following steps in the flowchart shown in FIG. 4 are implemented.

If on the other hand the capacity of the memory 16 is insufficient as represented by a YES at decision step S31, then the processing proceeds to step S32, wherein an alarm sound or alarm message is generated. In the next step S33, the ending track number of the immediately-preceding program is corrected by the ending track number ETN of the final program. It is determined in the next decision step S34 whether or not date data of the final program and date data of the immediately-preceding program agree with each other.

If date data do not agree with each other as represented by a NO at decision step S34, then the processing proceeds to step S35, the date data of the immediately-preceding program is made invalid. If date data agree with each other as represented by a YES at decision step S34, the date data of the immediately-preceding program is not changed.

Then, the processing proceeds to step S36, wherein data of the final program is erased. Then, the starting track number BTN of the new program is generated and recorded in the starting track number of the final program. Thereafter, the processing returns to the step S4 of the flowchart shown in FIG. 4.

Figure 11A:
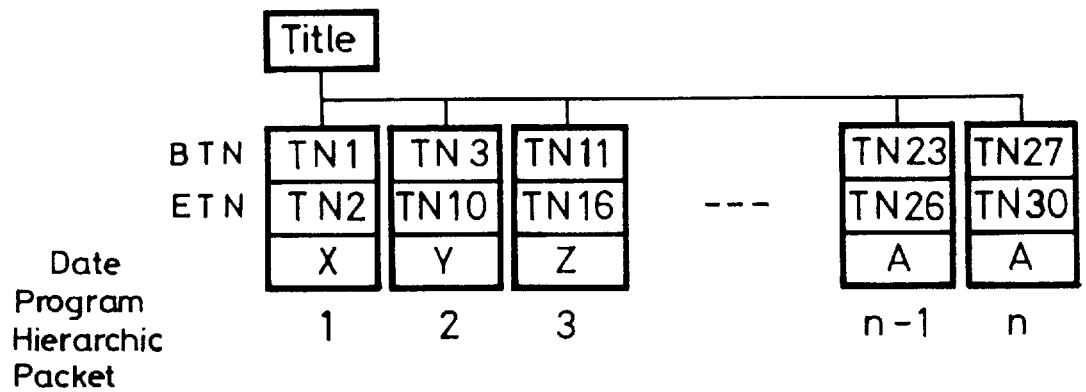
FIG. 11A through 11C are diagrams used to explain the operation of the flowchart shown in FIG. 10, respectively.
Figure 11B:
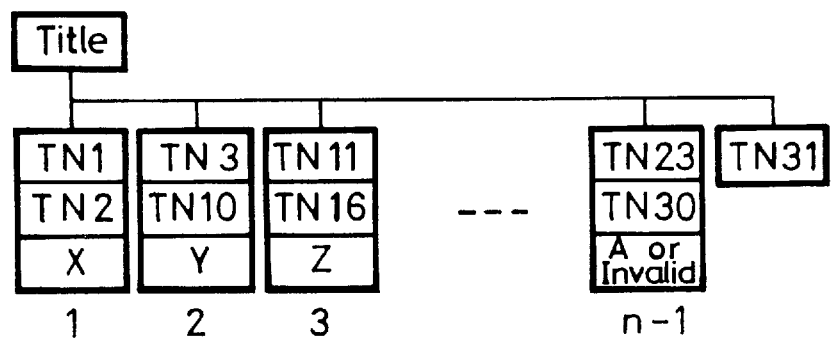

Therefore, if the state shown in FIG. 11A is presented and the capacity of the memory 16 is insufficient, at a timing point at which the new recording is started, as shown in FIG. 11B, the ending track number TN26 of the immediately-preceding program hierarchic packet n−1 is corrected by the ending track number TN30 of the final program hierarchic packet n and the new recording starting track number TN31 is recorded on the starting track number BTN of the final program.

Figure 11C:
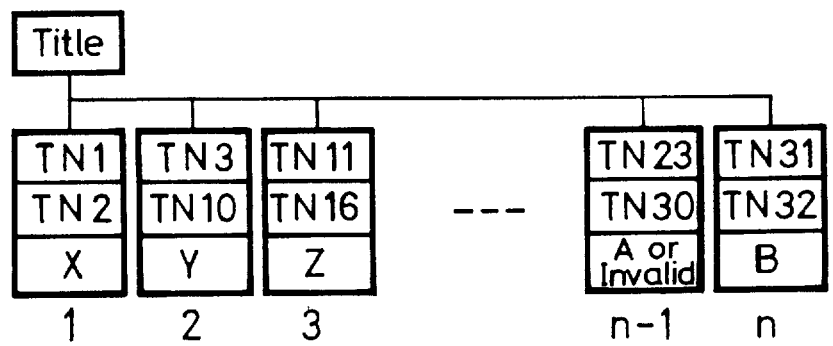

When the new recording is completed, as shown in FIG. 11C, a new recording ending track number TN32 is generated, and this ending track number TN32 is recorded on the ending track number ETN of the final program hierarchic packet n. Also, the date data from the calendar circuit 17 is recorded on the final program hierarchic packet n.

Therefore, according to the above-mentioned method of the present invention, when the capacity of the recording medium is insufficient, after the alarm sound or alarm message is generated, the processing smoothly executes the editing of the previously-recorded video information.

Further, according to the above method, the processing to be executed when the capacity of the video information recording medium (memory 16) is insufficient can be implemented in accordance with the clock information from the clock circuit 18, the place information from the GPS circuit 19 and the information from the scene setting switch 20 of the operation unit 12 instead of the date information from the calendar circuit 17.

Furthermore, according to the processing of other example shown in the flowchart of FIG. 10, it is possible to smoothly carry out the recording confirmation processing shown in the flowchart of FIG. 7.

According to the present invention, since the recorded video information data are compared and video information is edited and recorded in response to a compared result, it becomes possible to record video information in a small capacity memory for a long period of time.

According to the present invention, since highly consecutive video information are edited into one video information by using date information, clock information, place information or other information supplied from the operation unit, it is possible to use video information satisfactorily.

Further, since latest information is recorded separately, recorded content can be confirmed easily at any time. When a capacity of a recording medium is not sufficient, the processing smoothly executes the editing of the previously recorded video information after an alarm is generated.

Furthermore, the edit can be carried out by generating video information composed of a recording starting track number of previously-recorded video information and a recording ending track number of video information recorded later.

Having described a preferred embodiment of the invention with reference to the accompanying drawings, it is to be understood that the invention is not limited to the precise embodiment and that various changes and modifications could be effected therein by one skilled in the art without departing from the spirit or scope of the invention as defined in the appended claims.

What is claimed is:

1. A video information recording method for recording video information packets each having its contents composed of at least a recording starting track number, a recording ending track number and event information, comprising the steps of:
   comparing said event information contained in two previously recorded video information packets prior to recording a newly supplied video information packet;
   combining said two previously recorded video information packets into a common packet if the compared event information differs by less than a predetermined amount;
   replacing the contents of a first of said two previously recorded video information packets with the contents of said common packet; and
   recording the contents of said newly supplied video information packet in place of the contents of a second of said two previously recorded video information packets if it is determined that the compared event information differs by less than the predetermined amount.

2. The method of claim 1, wherein said event information is date information and said previously recorded video information packets are combined when the compared date information are equal.

3. The method of claim 1, wherein said event information is clock information and said previously recorded video information packets are combined when the compared clock information differ by a predetermined time period.

4. The method of claim 1, wherein said event information is place information and said previously recorded video information packets are combined when the compared place information differ by a predetermined range.

5. The method of claim 1, wherein said event information is information supplied from an operation unit and said previously recorded video information packets are combined when the content of the compared information supplied from said operation unit are equal.

6. The method of claim 1, wherein a latest supplied video information packet is stored separately from a previously recorded video information packet and said separately stored video information packets are compared when a new recording is started.

7. The method of claim 1, wherein the step of combining comprises generating a new video information packet from said two previously recorded video information packets such that a starting track number from one of said previously recorded video information packets and an ending track number from another of said previously recorded video information packets are included in said new video information packet.

8. A video information recording method for recording video information packets each having its contents composed of at least a recording starting track number, a recording ending track number and event information, comprising the steps of:

comparing said event information contained in two previously recorded video information packets prior to recording a newly supplied video information packet;

combining said two previously recorded video information packets into a common packet if the compared event information differs by less than a predetermined amount;

replacing the contents of a first of said two previously recorded video information packets with the contents of said common packet;

recording the contents of said newly supplied video information packet in place of the contents of a second of said two previously recorded video information packets if it is determined that the compared event information differs by less than the predetermined amount; and generating an alarm and combining a new video information packet with a previously recorded video information packet when a capacity of a recording medium in which said video information packets are recorded is insufficient.

9. An apparatus for recording on a tape cassette having a cassette housing for housing a first recording medium as a main recording medium and a second recording medium as a sub-recording medium, including:

control means for receiving information from a recording or reproducing apparatus, including video information packets each having its contents composed of at least a recording starting track number, a recording ending track number and event information, for comparing said event information contained in two previously recorded video information packets prior to recording a new supplied video information packet on said second recording medium, for combining said two previously recorded video information packets into a common packet if the compared event information differs by less than a predetermined amount, for replacing the contents of a first of said two previously recorded video information packets with the contents of said common packet; and recording means for recording the contents of said newly supplied video packet in place of the contents of a second of said two previously recorded video information packets if it is determined that the compared event information differs by less than the predetermined amount.

10. The apparatus of claim 9, wherein said event information is date information and said previously recorded video information packets are combined when the compared date information are equal.

11. The apparatus of claim 9, wherein said event information is clock information and said previously recorded video information packets are combined when the compared clock information differ by a predetermined time period.

12. The apparatus of claim 9, wherein said event information is place information and said previously recorded video information packets are combined when the compared place information differ by a predetermined range.

13. The apparatus of claim 9, wherein said event information is information supplied from an operation unit and said previously recorded video information packets are combined when the content of the compared information supplied from said operation unit are equal.

14. The apparatus of claim 9, wherein the newly supplied video information packet is stored separately from previously recorded video information packets and said separately stored video information packet is compared when a new recording operation is started.

15. The apparatus of claim 9, wherein said control means generates a new video information packet from said two previously recorded video information packets such that a starting track number from one of said previously recorded video information packets and an ending track number from another of said previously recorded video information packets are included in said new video information packet.

16. An apparatus for recording on a tape cassette having a cassette housing for housing a first recording medium as a main recording medium and a second recording medium as a sub-recording medium, including:

control means for receiving information from a recording or reproducing apparatus, including video information packets each having its contents composed of at least a recording starting track number, a recording ending track number and event information, for comparing said event information contained in two previously recorded video information packets prior to recording a new supplied video information packet on said second recording medium, for combining said two previously recorded video information packets into a common packet if the compared event information differs by less than a predetermined amount, for replacing the contents of a first of said two previously recorded video information packets with the contents of said common packet;

recording means for recording the contents of said newly supplied video packet in place of the contents of a second of said two previously recorded video information packets if it is determined that the compared event information differs by less than the predetermined amount; and information packet with a previously recorded video information packet when a capacity of said second recording medium in which said video information packet is recorded is insufficient.

* * * * *